(12) United States Patent
Cauldwell et al.

(10) Patent No.: US 10,405,858 B2
(45) Date of Patent: Sep. 10, 2019

(54) ACTUATION LOCKOUT FOR A SURGICAL INSTRUMENT

(71) Applicant: C.R. Bard, Inc., Murray Hill, NJ (US)

(72) Inventors: Nathan Stewart Cauldwell, Mansfield, MA (US); Kevin J. Ranucci, Warwick, RI (US)

(73) Assignee: C.R. Bard, Inc., Murray Hill, NJ (US)

( * ) Notice: Subject to any disclaimer, the term of this patent is extended or adjusted under 35 U.S.C. 154(b) by 726 days.

(21) Appl. No.: 14/755,347

(22) Filed: Jun. 30, 2015

(65) Prior Publication Data

US 2017/0000481 A1    Jan. 5, 2017

(51) Int. Cl.
  *A61B 17/068*    (2006.01)
  *A61B 17/29*    (2006.01)
  *A61B 90/00*    (2016.01)
  *A61B 17/064*    (2006.01)

(52) U.S. Cl.
  CPC .... *A61B 17/068* (2013.01); *A61B 2017/0649* (2013.01); *A61B 2017/2923* (2013.01); *A61B 2090/035* (2016.02)

(58) Field of Classification Search
  CPC ...... A61B 2017/2946; A61B 17/07207; A61B 17/068; A61B 2090/035; A61B 2017/0649; A61B 2017/2923
  USPC ...................................................... 227/175.2
  See application file for complete search history.

(56) References Cited

U.S. PATENT DOCUMENTS

| | | | |
|---|---|---|---|
| 5,258,010 A * | 11/1993 | Green | A61B 17/0682 227/176.1 |
| 5,665,105 A | 9/1997 | Furnish et al. | |
| 5,827,263 A | 10/1998 | Furnish et al. | |
| 5,997,552 A * | 12/1999 | Person | A61B 17/064 606/139 |
| 6,010,513 A * | 1/2000 | Tormala | A61B 17/064 606/142 |

(Continued)

FOREIGN PATENT DOCUMENTS

WO    WO 2016/000255    1/2016

OTHER PUBLICATIONS

International Search Report and Written Opinion for Application No. PCT/US2016/040018, dated Oct. 24, 2016.

(Continued)

*Primary Examiner* — Andrew M Tecco
(74) *Attorney, Agent, or Firm* — Wolf, Greenfield & Sacks, P.C.

(57) ABSTRACT

Surgical instruments and their methods of use are described. In one embodiment, a surgical instrument includes a power transmission including a trigger and a fastener driver operatively coupled to the trigger. Actuation of the trigger from a first configuration to a second configuration moves the fastener driver between at least a first position and a second position. Additionally, an actuation lockout system operatively associated with the power transmission is moveable between a locked configuration and an unlocked configuration. The actuation lockout system prevents movement of the fastener driver from the first position to the second position when the actuation lockout system is in the locked configuration. Actuation of the trigger from the first configuration towards the second configuration moves the actuation lockout system from the locked configuration to the unlocked configuration.

37 Claims, 8 Drawing Sheets

(56) References Cited

U.S. PATENT DOCUMENTS

| | | | |
|---|---|---|---|
| 6,042,601 A | 3/2000 | Smith | |
| 6,425,900 B1 | 7/2002 | Knodel et al. | |
| 6,457,625 B1 | 10/2002 | Toermaelae et al. | |
| 7,083,075 B2 * | 8/2006 | Swayze | A61B 17/07207 227/175.2 |
| 7,485,124 B2 * | 2/2009 | Kuhns | A61B 17/064 606/151 |
| 7,540,400 B2 | 6/2009 | Zins et al. | |
| 7,569,063 B2 | 8/2009 | Bailly et al. | |
| 7,771,440 B2 | 8/2010 | Ortiz et al. | |
| 7,832,612 B2 | 11/2010 | Baxter, III et al. | |
| 7,886,953 B2 | 2/2011 | Schwemberger et al. | |
| 7,905,893 B2 * | 3/2011 | Kuhns | A61B 17/064 606/151 |
| 7,931,660 B2 | 4/2011 | Aranyi et al. | |
| 8,403,944 B2 | 3/2013 | Pain et al. | |
| 8,424,737 B2 | 4/2013 | Scirica | |
| 8,683,895 B2 | 4/2014 | Nash et al. | |
| 8,684,247 B2 | 4/2014 | Scirica et al. | |
| 8,794,496 B2 | 8/2014 | Scirica | |
| 9,089,379 B2 | 7/2015 | Sack et al. | |
| 9,364,235 B2 | 6/2016 | Ranucci | |
| 9,526,498 B2 | 12/2016 | Reed | |
| 2008/0314958 A1 * | 12/2008 | Scirica | A61B 17/07207 227/175.2 |
| 2009/0236395 A1 | 9/2009 | Scirica | |
| 2009/0312603 A1 | 12/2009 | Lam et al. | |
| 2011/0130782 A1 | 6/2011 | Kan et al. | |
| 2012/0283739 A1 | 11/2012 | Ralph et al. | |
| 2013/0116710 A1 | 5/2013 | Ziniti et al. | |
| 2014/0263544 A1 | 9/2014 | Ranucci et al. | |
| 2014/0276963 A1 | 9/2014 | Ranucci et al. | |
| 2014/0326249 A1 | 11/2014 | Cappiello et al. | |
| 2015/0150558 A1 | 6/2015 | Zergiebel | |

OTHER PUBLICATIONS

International Search Report and Written Opinion for Application No. PCT/US2016/028585, dated Jul. 26, 2016.

* cited by examiner

ACTUATION LOCKOUT FOR A SURGICAL INSTRUMENT

FIELD

Disclosed embodiments are related to actuation lockouts for surgical instruments.

BACKGROUND

Oftentimes a surgical mesh fabric or other prosthetic repair fabric is used during a surgical repair of a hernia or other tissue defect. The prosthetic repair fabric may be placed in an open procedure or laparoscopically. To secure the repair fabric in place, one or more fasteners may be deployed through the prosthetic repair fabric and into the underlying tissue.

SUMMARY

In one embodiment, a surgical instrument includes a power transmission including a trigger and a fastener driver operatively coupled to the trigger. Actuation of the trigger from a first configuration to a second configuration moves the fastener driver between at least a first position and a second position. The surgical instrument further includes an actuation lockout system operatively associated with the power transmission. The actuation lockout system is moveable between a locked configuration and an unlocked configuration. The actuation lockout system prevents movement of the fastener driver from the first position to the second position when the actuation lockout system is in the locked configuration. Actuation of the trigger from the first configuration towards the second configuration moves the actuation lockout system from the locked configuration to the unlocked configuration.

In another embodiment, a surgical instrument includes a power transmission including a trigger and a fastener driver operatively coupled to the trigger. Actuation of the trigger from a first configuration to a second configuration moves the fastener driver between at least a first position and a second position. The surgical instrument further includes one or more locking surfaces associated with the fastener driver and a control surface moveable between a locked configuration and an unlocked configuration when the trigger is actuated from the first configuration towards the second configuration. The control surface obstructs motion of at least one of the one or more locking surfaces to prevent motion of the fastener driver between the first position and the second position when the control surface is in the locked configuration.

In a further embodiment, a method of operating a surgical instrument includes: initially restraining movement of a fastener driver operatively associated with a trigger using an actuation lockout system; actuating the trigger from a first configuration towards a second configuration; moving the actuation lockout system from a locked configuration to an unlocked configuration in response to said actuating of the trigger; and moving the fastener driver from a first position to a second position when the actuation lockout system is in the unlocked configuration.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings.

DETAILED DESCRIPTION

The inventors have realized the benefits associated with providing a surgical instrument that includes an actuation lockout system that restrains and/or prevents movement of a fastener driver until fastener deployment is desired. The inventors have recognized that typical actuation lockout systems require an active step from a user to unlock the system, such as flipping a separate safety switch, before a surgical device can be actuated. Such active steps can be cumbersome, confusing, and/or inconvenient. Therefore, in some instances, it may be desirable to unlock an actuation lockout system without requiring a separate step from the user. Therefore, the inventors have recognized advantages associated with an actuation lockout system that moves from a locked configuration to an unlocked configuration as a trigger is actuated. Such a system eliminates the need for any additional actions by the user to unlock the device, thereby providing a surgical instrument that is easier and/or more intuitive to operate, and that provides functionality regardless of whether or not a user remembers to engage/disengage the actuation lockout system.

In some embodiments, a surgical instrument includes a power transmission with a trigger operatively coupled to a fastener driver. The power transmission transfers force applied to the trigger by a user to the fastener driver, which deploys a fastener from a distal end of the surgical instrument. The power transmission may include any number of components between the trigger and the fastener driver arranged in any suitable manner. For example, components that may be included in a power transmission between the trigger and fastener driver include spur gears, helical gears, crown gears, worm gears, planetary gear systems, belts, clutch interfaces, linkages, or any other appropriate components capable of transmitting power from one component to another. Further, embodiments in which the trigger is directly coupled to the fastener driver, as well as embodiments in which the trigger is not coupled to the fastener driver (e.g., motor driven surgical instruments) are also contemplated as the disclosure is not so limited.

Further, it should be understood that the current disclosure is not limited to any particular type of fastener driver. For example, the fastener driver may be rotationally and/or linearly displaceable for imparting a deployment force to a surgical fastener. In some embodiments, the fastener driver is a rotator formed as a hollow tube and includes fasteners disposed inside the distal end of the fastener driver. Alternatively, the fastener driver may be a solid rod or shaft and may include fasteners disposed on an outer surface of the fastener driver such that rotation and/or linear movement of the fastener driver displaces the fasteners. In yet other embodiments, the fasteners may be located distally relative to a distal end of the fastener driver such that the distal end of the fastener driver engages with and deploys the fasteners when the fastener driver moves rotationally and/or linearly. Accordingly, it should be understood that a fastener driver may include any structure capable of transferring a deployment force to a fastener as the disclosure is not limited to any particular arrangement.

Depending on the particular embodiment, the fastener driver may be arranged to deploy fasteners rotationally and/or linearly; therefore the power transmission and fastener driver may be configured to provide a corresponding rotational and/or linear force to the fasteners. In one such embodiment, actuating a trigger from a first configuration to a second configuration moves the fastener driver from a first position to a second position. For example, in the case of a rotationally deployed fastener, the fastener driver moves between a first and second rotational position such that rotation of the fastener driver imparts a rotational force to the fastener. Alternatively, in the case of a linearly deployed fastener, the fastener driver moves distally from a first proximal position to a second distal position such that the fastener driver applies a distally directed force to the fastener. In further embodiments, the fastener driver may move both rotationally and linearly to deploy a fastener. Consequently, it should be understood that the current disclosure is not limited to any particular displacement direction of the fastener driver such that the fastener driver may be displaced axially, rotationally, a combination of the two, or in any other appropriate fashion.

As noted above, a surgical instrument may include an actuation lockout system to prevent actuation of the surgical instrument until the trigger is actuated. The actuation lockout system may be associated with any portion of the power transmission, including the trigger, fastener driver, and/or any intermediate component located between the two. Additionally, the actuation lockout system may selectively prevent movement of the fastener driver that may result, for example, from vibrations, handling, transport of the surgical instrument, or other sources. By preventing unwanted movements of the fastener driver, the actuation lockout system also prevents associated movement of the surgical fasteners.

In some embodiments, an actuation lockout system is moveable between a locked configuration, in which movement of the fastener driver is restrained, and an unlocked configuration in which the fastener driver is free to move to deploy a surgical fastener. In one such embodiment, the actuation lockout system is associated with an appropriate portion of the power transmission such that actuation of the trigger moves the actuation lockout system from the locked to the unlocked configuration. For example, the trigger may be movable between a first initial or unactuated configuration and a second actuated configuration corresponding to a surgical fastener being deployed from the surgical instrument. In the above described system, the actuation lockout system is configured to be in the locked configuration when the trigger is in the first configuration. Moving the trigger from the first configuration towards the second configuration moves the actuation lockout system from the locked configuration to the unlocked configuration such that the fastener driver may be displaced (e.g., rotationally and/or linearly) to deploy a fastener.

In some embodiments, the actuation lockout system includes a control surface associated with the trigger and one or more locking surfaces associated with the fastener driver. The one or more locking surfaces are operatively coupled with the fastener driver such that blocking movement of the one or more locking surfaces prevents movement of the fastener driver. The locking surfaces may either be directly coupled with the fastener driver, or they may be coupled with another part of the power transmission, as the disclosure is not limited to which specific part the locking surfaces are positioned on. Regardless of their specific location, when the actuation lockout system is in the locked configuration, the control surface is aligned with a path of travel of at least one of the locking surfaces. In this manner, the control surface obstructs and/or interferes with movement of the locking surface to prevent associated movement of the fastener driver. As described above, actuation of the trigger moves the actuation lockout system from the locked configuration to the unlocked configuration. In one embodiment, moving the actuation lockout system to the unlocked configuration includes moving the control surface out of alignment with the path of travel of the locking surfaces such that the control surface no longer interferes with and/or obstructs motion of the locking surfaces. In other embodiments, moving the actuation lockout system to the unlocked configuration includes moving the locking surfaces relative to the control surface, or alternatively moving both the control surface and the locking surfaces, to a configuration in which the control surface does not obstruct motion of the one or more locking surfaces. Once the one or more locking surfaces are free to move, the fastener driver is able to be displaced to deploy a fastener.

It should be understood that the control and/or locking surfaces in an actuation lockout system may include any suitable combination of corresponding surfaces that interact with one another to selectively block movement of the locking surfaces when they are aligned with one another. For example, the control and/or locking surfaces may include any appropriate combination of tabs, shoulders, cut outs, pins, grooves, slots, lips, protrusions, or any other suitable structure. In one such embodiment, the control and locking surfaces include two corresponding tabs that are brought into and out of alignment to move the system into and out of a locked configuration. In another embodiment, the control and locking surfaces include a pin or similar projecting structure that is positioned in a corresponding structure capable of capturing the pin such as a groove, slot, or hole that is sized, shaped, and oriented, to prevent movement of the pin in a particular direction. Moving the pin into and out of engagement with the corresponding structure selectively permits motion of the associated fastener driver. In yet another embodiment, the locking surface is a shoulder on the fastener driver, or other suitable portion of the power transmission. The control surface includes a corresponding pin, shoulder, block, or any other structure that is capable of selectively interfering with movement of the shoulder to move the actuation lockout system between the locked and unlocked configurations.

In view of the above, it should be understood that the current disclosure is not limited to any particular type or combination of control and locking surfaces. Therefore, the control and locking surfaces may include any suitable combination of structures that may be selectively aligned and/or engaged with one another to selectively block and/or restrict motion of a fastener driver.

Depending on the particular embodiment, the control surface and the one or more locking surfaces may move into and out of alignment in any suitable fashion when the actuation lockout system moves between the locked and unlocked configurations. Therefore, the actuation lockout system may include any suitable mechanism capable of moving the control surface into and out of alignment with the one or more locking surfaces when the trigger is actuated. For example, in one embodiment, the control surface is directly coupled to the trigger such that movement of the trigger moves the control surface into and out of alignment with the locking surfaces. Alternatively, the control surface may be indirectly coupled to the trigger. For example, the control surface may be coupled to the trigger via one or more gears, one or more links, a rack and pinion configuration, complementary camming surfaces, or any other structure capable of transferring motion of the trigger to motion of the control surface. In one such embodiment, the control surface is disposed on the face of a gear that is coupled to the trigger either directly, or through one or more intermediate gears. Actuation of the trigger from the first configuration towards the second configuration drives rotation of the gear to rotate the control surface out of alignment with the path of travel of the one more locking surfaces. In another embodiment, and as described further below in the figures, the control surface is disposed on a first link operatively coupled to the trigger. Actuation of the trigger moves the first link linearly and/or rotationally relative to the associated locking surfaces.

While several possible configurations have been described related to different embodiments for controlling the relative positioning of the locking and control surfaces of an actuation lockout system, it should be understood that the actuation lockout systems described herein are not limited to any particular arrangement for controlling the relative movement of a locking and control surface. For example, although a control surface has been described as moving out of alignment with the locking surfaces, in other embodiments, the locking surfaces may move relative to a stationary control surface, or alternatively both the control surface and locking surfaces may move relative to each other when the actuation lockout system moves between the locked and unlocked configurations. Further, the locking and/or control surfaces may move relative to each other in any desired manner including, but not limited to, linearly, rotationally, a combination of linearly and rotationally, as well as along a non-linear path such as a curve to name a few.

It is also noted that the various embodiments of an actuation lockout system disclosed herein are not limited to use with any particular type of fastener or surgical instrument. For example, an actuation lockout system could be used with a tack, clip, staple, pin, tissue anchor, bone anchor, coil fasteners, screw fasteners, and any other type of fastener that could benefit from the use of an actuation lockout system to avoid incomplete and/or unintentional deployment of a fastener. Similarly, the actuation lockout system may be used in any number of medical procedures including, but not limited to, attaching a repair fabric or mesh to underlying tissue, attaching adjacent layers of tissue, attaching identification devices and/or tags to livestock, and other appropriate applications involving the deployment of a fastener.

For the sake of clarity, the embodiments described in relation to the figures are directed to a laparoscopic fastening instrument. However, the current disclosure is not so limited. Instead, the actuation lockout system could be incorporated in any actuated surgical instrument. For example, an actuation lockout system could be employed in an endoscopic device, a borescopic device, a catheter, a surgical instrument for use in "open" procedures, surgical instruments including actuated working tools, or any other appropriate surgical instrument. In embodiments in which the surgical instrument deploys fasteners, the surgical instrument may be constructed to allow the user to load the instrument with one or more fasteners, be preloaded with one or more fasteners, be selectively connected with a disposable loading unit including one or more preloaded fasteners, or be constructed in any other appropriate manner.

Turning now to the figures, specific non-limiting embodiments of actuation lockout systems and surgical instruments are described in further detail.

Figure 1:
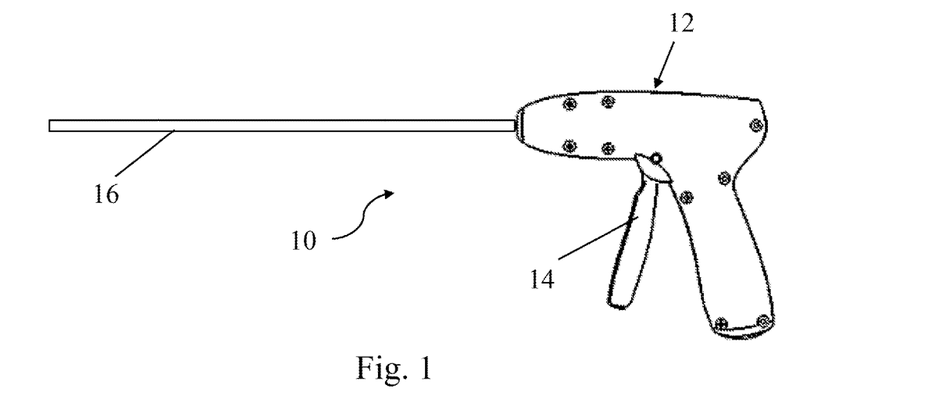
FIG. 1 is a schematic representation of a surgical instrument.

FIG. 1 depicts a surgical instrument 10 for deploying one or more surgical fasteners. The surgical instrument 10 includes a handle 12 at a proximal end of the device and a trigger 14. The surgical instrument also includes an outer elongated shaft 16 extending in a distal direction from the handle. When the trigger is actuated, a surgical fastener is deployed from a distal tip of the elongated shaft. It should be understood that the deployed surgical fastener may be deployed into any appropriate prosthetic, bone, and/or tissue. For example, in one embodiment, a surgical fastener can be deployed into a soft tissue repair fabric, such as a surgical mesh, as well as into underlying tissue for repairing a hernia.

Figure 2:
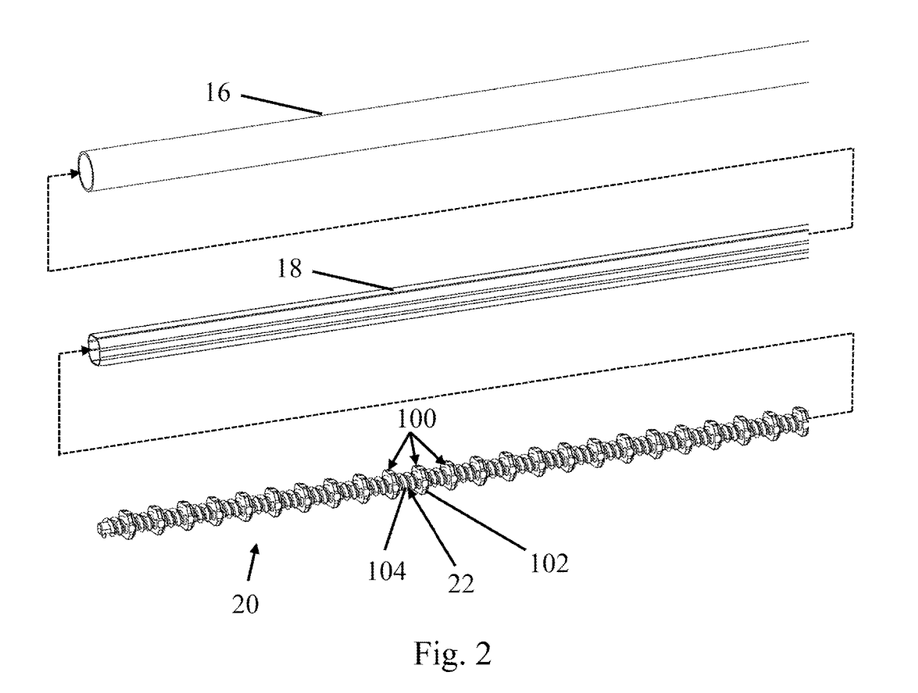
FIG. 2 is an exploded view of the distal end of the surgical instrument of FIG. 1.

FIG. 2 depicts an exploded view of the distal end of the surgical instrument 10 of FIG. 1. As depicted in the figure, the surgical instrument includes an outer elongated shaft 16, a rotator 18, and a mandrel 20. When assembled, the mandrel is disposed within the rotator, which is disposed within the outer elongated shaft. In the depicted embodiment, the rotator is a rotatable drive tube and the mandrel includes a threaded portion 22 for supporting one or more surgical fasteners 100. As shown in the figures, the surgical fasteners may be coil fasteners with a head 102 including a through hole to receive the threaded mandrel and a coil body 104. As described in more detail below, the trigger is coupled to the rotator via a power transmission, not depicted, such that actuation of the trigger rotates the rotator relative to the mandrel. Rotation of the rotator rotates the surgical fasteners disposed on the threaded portion of the mandrel, which displaces the fasteners in a distal direction and deploys the distal most fastener into a prosthetic and/or tissue. A more detailed description of this type of fastener deployment system is provided in U.S. application Ser. No. 14/075,398 filed Nov. 8, 2013, published as US2015/0133964, which is incorporated herein for all purposes.

Figure 3:
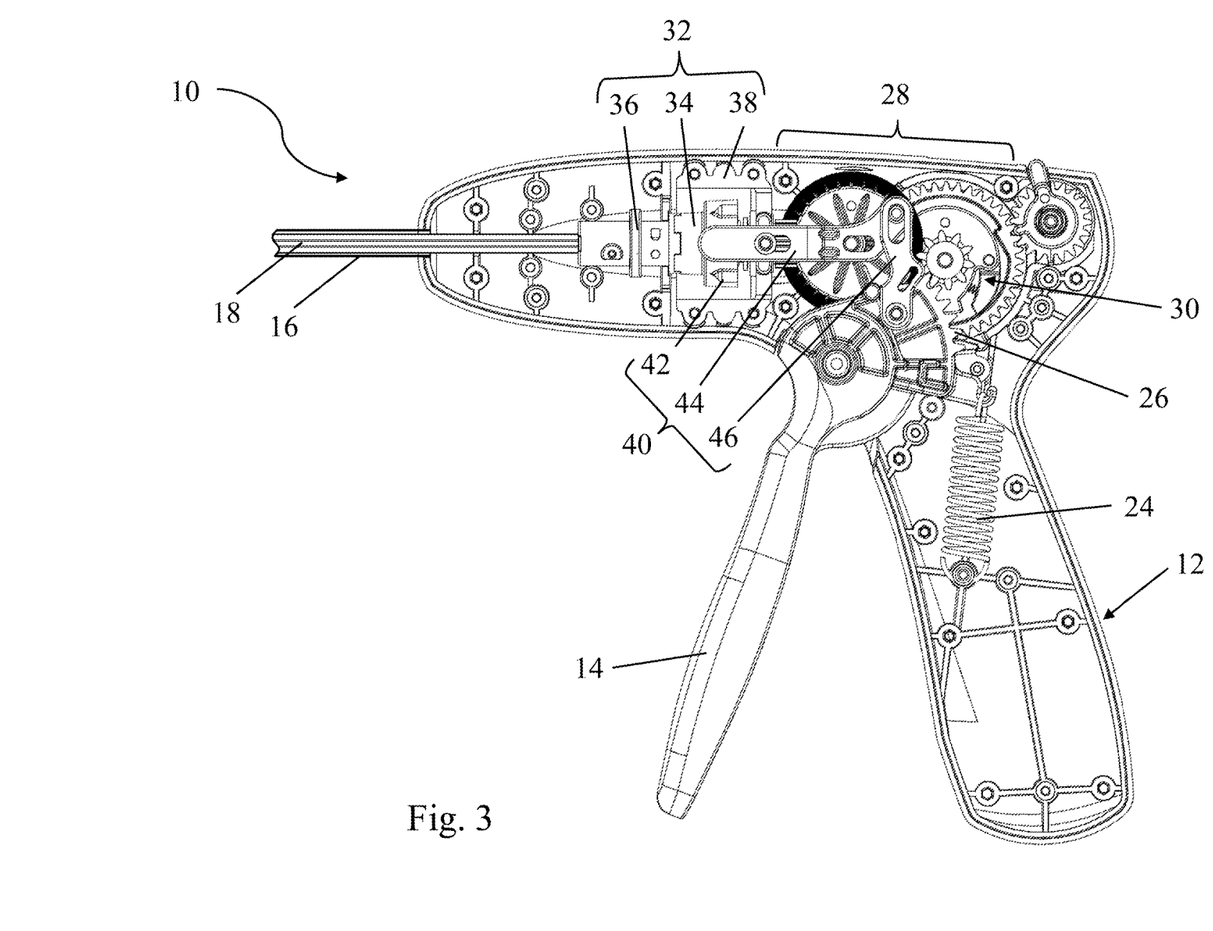
FIG. 3 is a cross-sectional view of the a surgical instrument handle including an actuation lockout system.

Referring now to FIG. 3, the components within an interior of one embodiment of a surgical instrument 10 are described in more detail. As illustrated in the figure, the surgical instrument includes a trigger 14 and a return spring 24 attached to both the trigger and the handle 12. The return spring provides a restoring force to assist in returning the trigger to an initial, unactuated configuration when the trigger is in an actuated configuration. The trigger includes teeth 26 configured to engage a corresponding gear of a power transmission 28. In the depicted embodiment, the power transmission includes a gear train arranged to convert movement of the trigger into rotational motion of the rotator 18 to deploy a fastener, as well as a unidirectional gear clutch 30 arranged to limit the rotator to rotate in a single direction during both the actuation and subsequent release of the trigger. As described in more detail below, the surgical instrument further includes a rotation coupling 32 to allow an operator to selectively rotate the rotator and adjust the position of a fastener. The surgical instrument also includes an actuation lockout system 40 to restrict movement of the rotator 18 until the trigger is actuated; additional details of the actuation lockout system are described below with reference to FIGS. 4-9.

Although a power transmission including a plurality of gears is depicted and described above, it should be understood that other mechanisms or configurations also may be used to transfer a force applied to the trigger to the rotator or other fastener driver. For example, linkages may be used to transfer a displacement of the trigger to an associated displacement of the fastener driver. Such a configuration may be beneficial for embodiments employing a linearly displaced fastener driver. Alternatively, the trigger may be directly coupled to the fastener driver via a pin joint, rack and pinion configuration, or any other suitable structure.

In some embodiments, it may be advantageous to limit the movement of a rotatable fastener driver to a single rotational direction to help ensure complete deployment of a fastener and to avoid back out of the fastener after it is deployed. Therefore the power transmission may include a one way gear clutch mechanism that only provides a rotational force in a single direction. In the depicted embodiment, the gear clutch mechanism 30 includes shoulders that engage with a moveable arm when the gear clutch is rotated in a direction corresponding to deployment of a fastener. A biasing element is associated with the arm to help the arm engage with the shoulders. When the clutch gear is rotated backwards, for example when the trigger moves from the second (actuated) configuration back to the first (unactuated) configuration, camming surfaces on the clutch deflect the arm over the shoulders such that the arm does not engage with the shoulders to drive rotation of the fastener driver. In some embodiments, the power transmission further includes a ratchet that is configured to only allow the gear train to rotate in a single direction to further aid in avoiding undesirable back out of a fastener.

Figure 4:
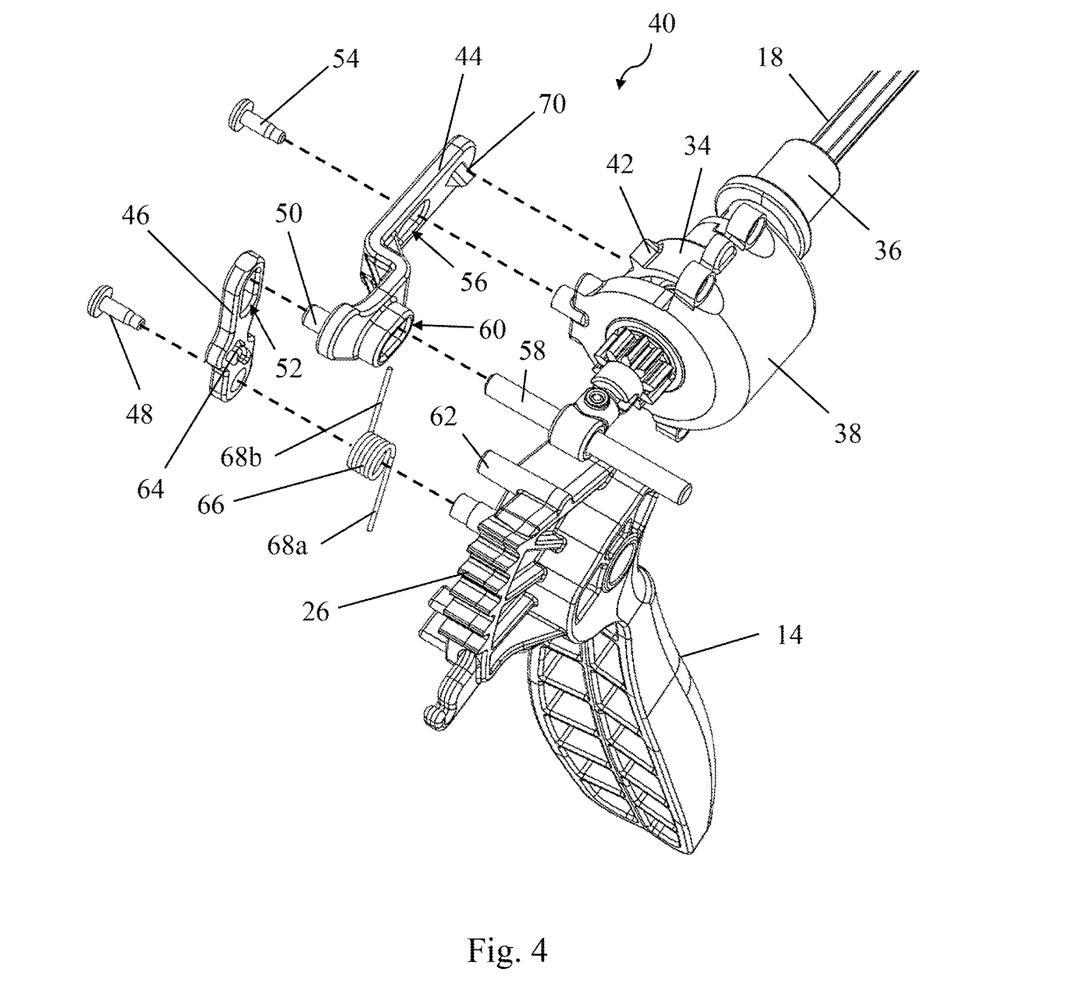
FIG. 4 is an exploded view of an actuation lockout system.

FIG. 4 is an exploded view of the actuation lockout system 40 of FIG. 3. For the purpose of clarity, many components of the surgical instrument, including the handle and power transmission, are not depicted. The actuation lockout system includes a control tab 70 and a plurality of locking tabs 42. In this embodiment, the control tab is integrally formed in a movable link as described below. Further, the locking tabs are disposed on, extend outwardly from, and are distributed circumferentially around the outer surface of a first half 34 of a rotation coupling 32. As described below, the rotation coupling couples the trigger to the rotator 18. While corresponding locking and control tabs are depicted in the figures and described above, it should be understood that any suitable combination of control and locking surfaces may be used instead as the disclosure is not so limited.

As illustrated in the depicted embodiment, the position of the control tab 70 is controlled by a linkage coupled to the trigger 14. The linkage includes a first link 44, on which the control tab is disposed. The first link includes a first channel 56 and a second channel 60 in which a first pin 54 and an axle 58 are received, respectively. The first pin is attached to a housing 38 of the rotation coupling, and the axle is attached to the handle. In this manner, the channels, first pin, and axle define a translation path for the first link, which in turn defines a translation path for the control tab 70 disposed on the first link. In the depicted embodiment, the first and second channels are arranged such that the first link and the control tab reciprocate proximally and distally along a path that is substantially parallel to an axial direction of the rotator. However, it should be understood that in other embodiments, the first link and control tab may be arranged to displace in a direction transverse to the rotator, or in any other suitable direction, as the present disclosure is not so limited.

The linkage also includes a second link 46 that couples the trigger to the first link 44. The second link is coupled to the first link via a second pin 50 connected to the first link. The second pin is received in an elongated slot 52 formed in an end of the second link. Further, an opposing end of the second link is directly coupled to the trigger via a biased pin joint including a third pin 48 and torsion spring 66. The torsion spring has a first end 68a that is coupled to a portion of the trigger and a second end 68b that is received by a hook 64 disposed on the second link. Consequently, the torsion spring provides a rotational bias to the second link, which facilitates movement of the actuation lockout system from the locked configuration to the unlocked configuration, as described in more detail below. Although a torsion spring is depicted, it should be understood that the current disclosure is not limited to a specific type of biasing element. In other embodiments, other biasing elements, such as compression springs, elastic rods or bands, elastic arms, or any other structure capable of biasing the second link in an appropriate direction may be used.

Figure 5:
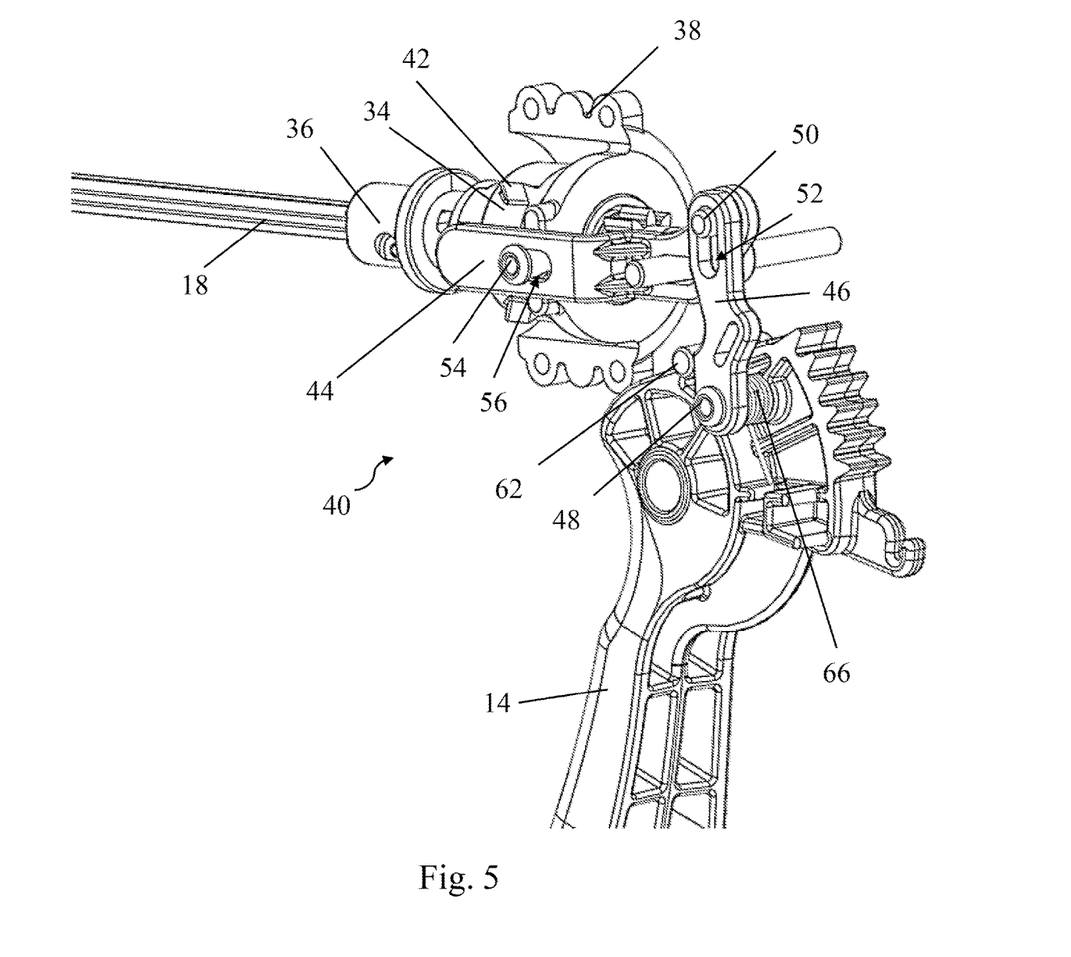
FIG. 5 is a perspective view of the actuation lockout system of FIG. 4 in a locked configuration.
Figure 6:
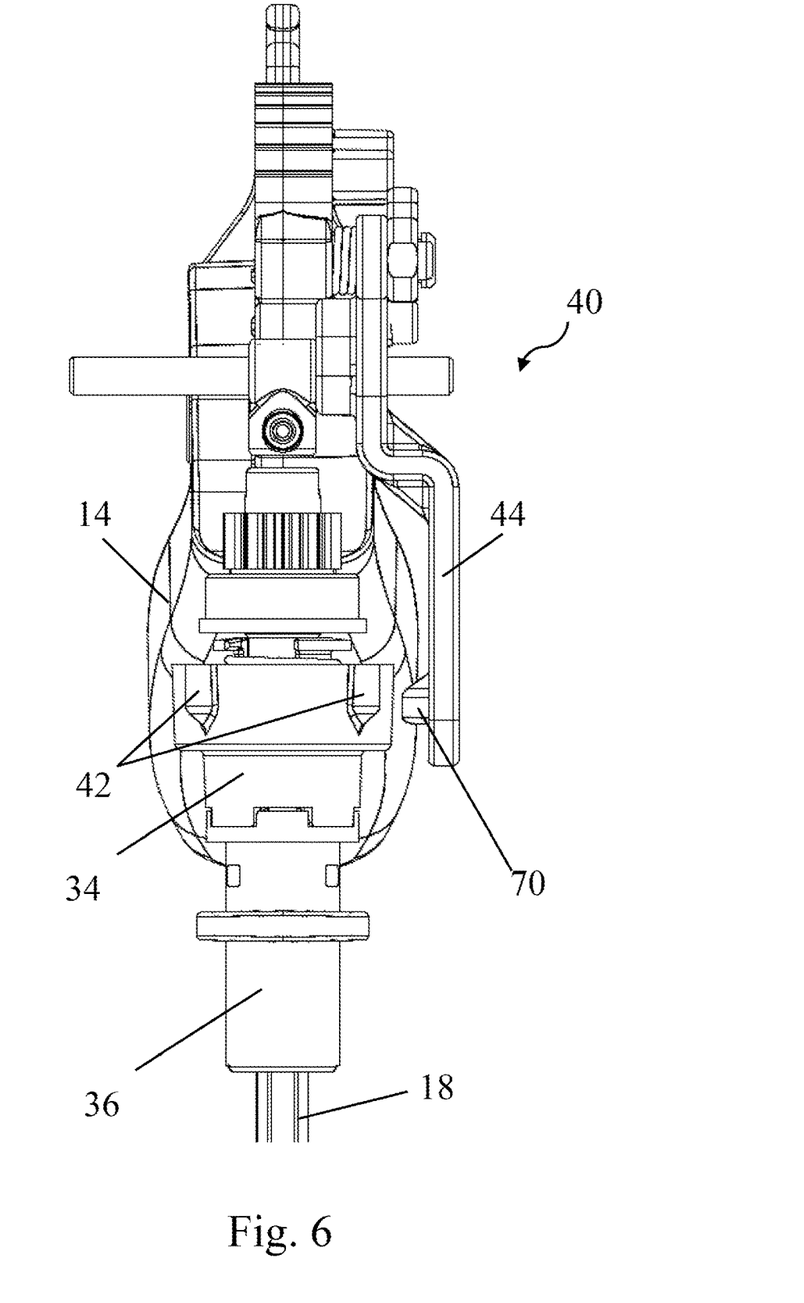
FIG. 6 is a top view of the actuation lockout system of FIG. 4 in a locked configuration.

Having described the various components of the actuation lockout system 40, its method of use is described in more detail with reference to FIGS. 5-8. FIGS. 5-6 depict an actuation lockout system 40 in the locked configuration, i.e., before actuation of the trigger 14. In the locked configuration, movement of the second link 46 due to the biasing force from the torsion spring 66 is limited by a control pin 62 to prevent the actuation lockout system from moving to the unlocked configuration before actuation of the trigger. As illustrated in FIG. 6, when the actuation lockout system is in the locked configuration, the control tab 70 is aligned with a path of travel of the locking tabs 42 to block movement of the locking tabs. Therefore, the rotator, which is associated with the locking tabs, is also restrained from moving.

Figure 7:
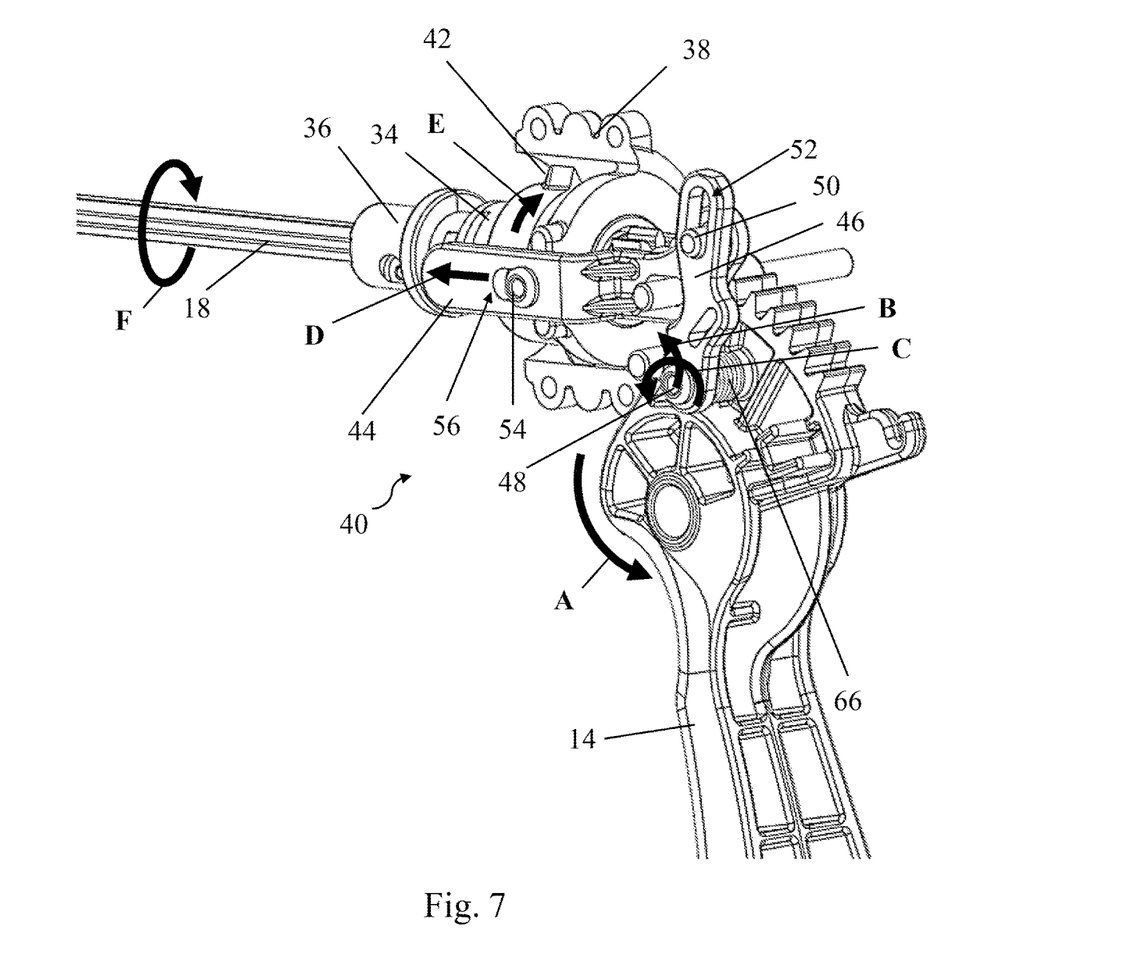
FIG. 7 is a perspective view of the actuation lockout system of FIG. 4 in an unlocked configuration.
Figure 8:
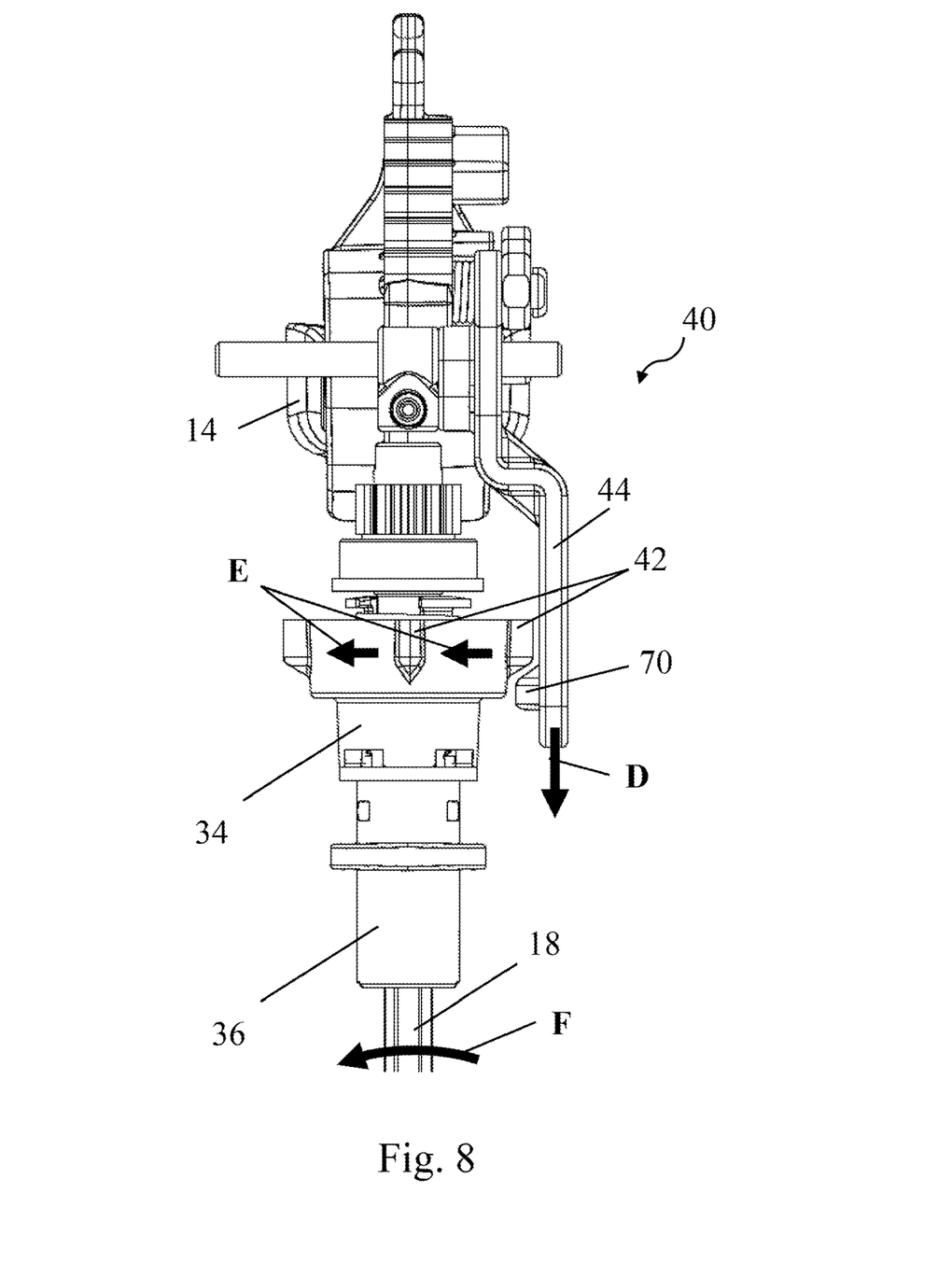
FIG. 8 is a top view of the actuation lockout system of FIG. 4 in an unlocked configuration.

FIGS. 7-8 depict an actuation lockout system 40 in the unlocked configuration. Actuation of the trigger 14 along direction A from a first configuration (e.g., an unactuated configuration) towards a second configuration (e.g., an actuated configuration in which a fastener is fully deployed) causes an associated displacement of the second link 46 in direction B, and the torsion spring 66 provides a rotational biasing force about the third pin 48 in direction C to urge the actuation lockout system towards the unlocked configuration. Specifically, the rotational force is transferred to the first link 44 via the second pin 50 received in slot 52, and therefore provides a linear force to the first link, which in turn, causes displacement of the first link in direction D. As illustrated in FIG. 7, translation of the first link moves the control tab 70 out of alignment with a path of travel of the locking tabs 42 such that the locking tabs are free to move in direction E during subsequent portions of the actuation cycle. As a result, the rotator 18 is also free to rotate as shown by arrow F.

Rotation of the locking tabs (disposed on the first half 34 of the rotation coupling) and the associated rotator is driven by the power transmission (not depicted). When the trigger moves from the second position back towards the first position, for example due to a biasing force provided by the return spring 24, the motion of the first and second links are reversed to move the actuation lockout system back into the locked configuration. Therefore, the process of initially restricting and subsequently permitting rotation of the rotator occurs during each actuation of the surgical instrument.

Figure 9:
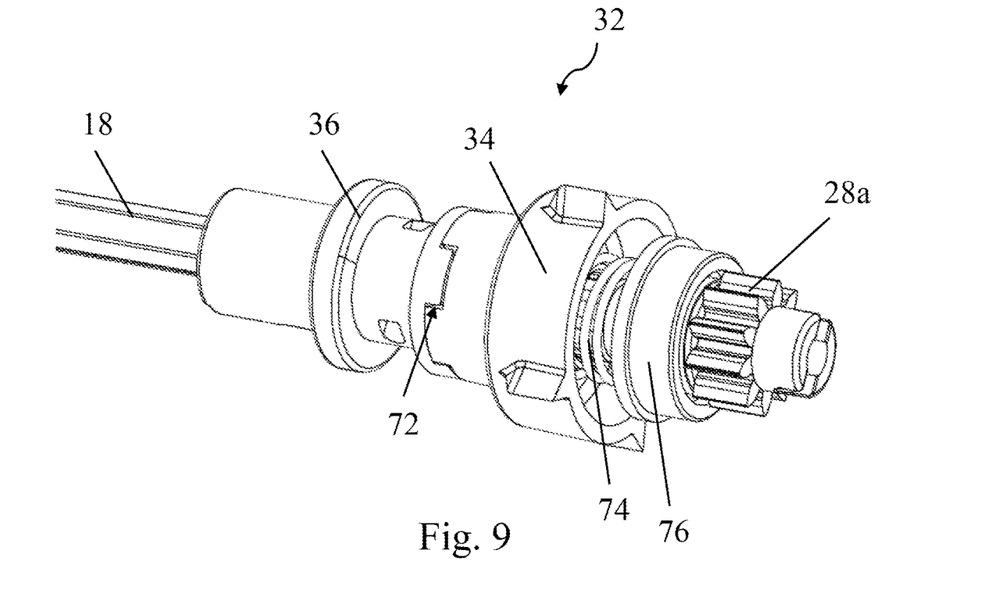
FIG. 9 is a perspective view of a rotation coupling in a coupled configuration.
Figure 10:
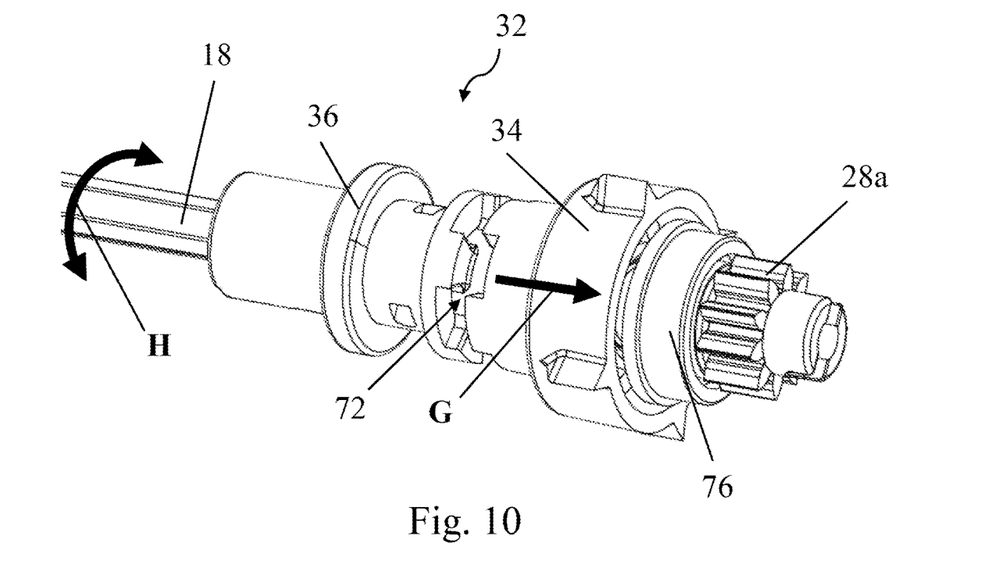
FIG. 10 is a perspective view of the rotation coupling of FIG. 9 in a decoupled configuration.

To ensure appropriate positioning of a stack of surgical fasteners positioned within a surgical instrument during manufacture, it may be desirable to permit the rotation of a rotatable fastener driver without requiring full disassembly of the instrument. Therefore, and as described above, in some embodiments, a surgical instrument includes a rotation coupling that selectively allows rotation of the rotator 18, or other appropriate fastener driver, to adjust the position of the fasteners 100 along a mandrel 20. For example, FIG. 9 depicts one embodiment of a rotation coupling 32 in a coupled configuration such that a rotational force from the power transmission is transferred through the rotation coupling to the rotator. In the depicted embodiment, the rotation coupling includes a first half 34 coupled to the power transmission, and a second half 36 coupled to the rotator. The first half of the coupling is coupled to a shaft gear 28a of the power transmission via a key fit (not depicted). The key fit forms a slidable connection between the first half of the coupling and the shaft gear such that the coupling may be slid both proximally and distally on the shaft gear. The first and second halves of the coupling interact with one another at an interface 74. In the depicted embodiment, the interface includes interlocking features, such as interlocking crenellated structures. However, it should be understood that the interface may correspond to any number of interfaces including, but not limited to, an interference fit, a nut and bolt connection, or any other suitable structure capable of transferring a rotational force between the first half and the second half of the coupling and that may be selectively engaged and disengaged to couple and decouple a fastener driver from an associated trigger. In the depicted embodiment, a pre-compressed spring 74 is positioned between opposing surfaces of a roller bearing 76 and the first half of the coupling 34. Thus, the first half of the coupling is biased in a distal direction towards the second half of the coupling which corresponds to an engaged configuration. As illustrated in FIG. 10, when it is desired to decouple the rotator from the trigger for rotating the rotator, a user displaces the first half of the coupling in a proximally oriented direction G to move the interface 72 out of engagement. The rotator is then decoupled from the trigger and may be freely rotated in direction H to adjust the position of a stack of fasteners as required. Once appropriately positioned, the first half of the coupling is released. After being released, the first half of the coupling is then displaced distally by the biasing spring to reengage the interface between the coupling halves and recouple the rotator with the trigger.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. A surgical instrument comprising:
   a power transmission including a trigger and a fastener driver operatively coupled to the trigger, wherein actuation of the trigger from a first configuration to a second configuration moves the fastener driver between at least a first position and a second position, wherein the first position of the fastener driver is a first rotational position and the second position of the fastener driver is a second rotational position;
   an actuation lockout system operatively associated with the power transmission, the actuation lockout system moveable between a locked configuration and an unlocked configuration, wherein the actuation lockout system maintains the fastener driver in the first position when the actuation lockout system is in the locked configuration, and wherein actuation of the trigger from the first configuration towards the second configuration moves the actuation lockout system from the locked configuration to the unlocked configuration.

2. The surgical instrument of claim 1, wherein the first position is a proximal position and the second position is a distal position.

3. The surgical instrument of claim 1, wherein the actuation lockout system comprises:
   one or more locking surfaces associated with the fastener driver; and
   a control surface, wherein the control surface is aligned with a path of travel of the one or more locking surfaces when the actuation lockout system is in the locked configuration.

4. The surgical instrument of claim 3, wherein moving the actuation lockout system from the locked configuration to the unlocked configuration moves the control surface out of the path of travel of the one or more locking surfaces.

5. The surgical instrument of claim 4, wherein the control surface is disposed on a first link operatively coupled to the trigger.

6. The surgical instrument of claim 5, wherein actuation of the trigger from the first configuration towards the second configuration moves the first link to move the control surface out of the path of travel of the one or more locking surfaces.

7. The surgical instrument of claim 3, wherein the one or more locking surfaces extend outward relative to an axial direction of the fastener driver, wherein the control surface moves in a direction parallel to an axial direction of the fastener driver.

8. The surgical instrument of claim 3, wherein moving the actuation lockout system from the locked configuration to the unlocked configuration moves the locking surfaces out of alignment with the control surface.

9. The surgical instrument of claim 3, wherein the one or more locking surfaces and the control surface comprise corresponding tabs or shoulders.

10. The surgical instrument of claim 5, wherein the first link is linearly displaceable along a direction parallel to an axial direction of the fastener driver.

11. The surgical instrument of claim 1, wherein the first configuration of the trigger is an unactuated configuration and the second configuration of the trigger is a fully actuated configuration.

12. A surgical instrument comprising:
   a power transmission including a trigger and a fastener driver operatively coupled to the trigger, wherein actuation of the trigger from a first configuration to a second configuration moves the fastener driver between at least a first position and a second position, wherein the first position of the fastener driver is a first rotational position and the second position of the fastener driver is a second rotational position;

one or more locking surfaces associated with the fastener driver; and a control surface that is moved between a locked configuration and an unlocked configuration when the trigger is actuated from the first configuration towards the second configuration, wherein the control surface obstructs motion of at least one of the one or more locking surfaces to maintain the fastener driver in the first position when the control surface is in the locked configuration.

13. The surgical instrument of claim 12, wherein the control surface is aligned with a path of travel of the at least one of the one or more locking surfaces when the control surface is in the locked configuration.

14. The surgical instrument of claim 13, wherein moving the control surface to the unlocked configuration moves the control surface out of the path of travel of the at least one of the one or more locking surfaces.

15. The surgical instrument of claim 12, further comprising a first link operatively coupled to the trigger, wherein the control surface is disposed on the first link.

16. The surgical instrument of claim 15, wherein actuation of the trigger from the first configuration towards the second configuration moves the first link to move the control surface from the locked configuration to the unlocked configuration.

17. The surgical instrument of claim 16, further comprising a second link directly coupled to the trigger and the first link, wherein the second link transfers rotational motion of the trigger into movement of the first link relative to the fastener driver.

18. The surgical instrument of claim 12, wherein the first position is a proximal position and the second position is a distal position.

19. The surgical instrument of claim 12, wherein the one or more locking surfaces and the control surface comprise corresponding tabs or shoulders.

20. The surgical instrument of claim 12, wherein the one or more locking surfaces extend outward relative to an axial direction of the fastener driver, wherein the control surface moves in a direction parallel to an axial direction of the fastener driver.

21. The surgical instrument of claim 12, wherein the first configuration of the trigger is an unactuated configuration and the second configuration of the trigger is a fully actuated configuration.

22. A surgical instrument comprising:
a power transmission including a trigger and a fastener driver operatively coupled to the trigger, wherein the fastener driver is rotatable about a longitudinal axis of the fastener driver, wherein actuation of the trigger from a first configuration to a second configuration moves the fastener driver between at least a first rotational position about the longitudinal axis of the fastener driver and a second rotational position about the longitudinal axis of the fastener driver;

an actuation lockout system operatively associated with the power transmission, the actuation lockout system moveable between a locked configuration and an unlocked configuration, wherein the actuation lockout system prevents movement of the fastener driver from the first rotational position to the second rotational position when the actuation lockout system is in the locked configuration; and a rotation coupling including a first coupling member operatively coupled to the trigger and a second coupling member operatively coupled to the fastener driver, wherein the first and second coupling members are moveable relative to one another between an engaged configuration in which the fastener driver is coupled to the trigger and a disengaged configuration in which the fastener driver is decoupled from the trigger.

23. The surgical instrument of claim 22, wherein the rotation coupling further comprises a spring configured to bias the first and second coupling members towards the engaged configuration.

24. The surgical instrument of claim 22, wherein the actuation lockout system comprises:
one or more locking surfaces associated with the fastener driver; and
a control surface, wherein the control surface is aligned with a path of travel of the one or more locking surfaces when the actuation lockout system is in the locked configuration.

25. The surgical instrument of claim 24, wherein the one or more locking surfaces extend outward relative to an axial direction of the fastener driver, wherein the one or more locking surfaces are distributed circumferentially around the first coupling member, and wherein the control surface moves in a direction parallel to an axial direction of the fastener driver.

26. A surgical instrument comprising:
a power transmission including a trigger and a fastener driver operatively coupled to the trigger, wherein actuation of the trigger from a first configuration to a second configuration moves the fastener driver between at least a first position and a second position, wherein the first configuration of the trigger is an unactuated configuration and the second configuration of the trigger is a fully actuated configuration;

an actuation lockout system operatively associated with the power transmission, the actuation lockout system moveable between a locked configuration and an unlocked configuration, wherein the actuation lockout system maintains the fastener driver in the first position when the actuation lockout system is in the locked configuration, and wherein actuation of the trigger from the first configuration towards the second configuration moves the actuation lockout system from the locked configuration to the unlocked configuration.

27. The surgical instrument of claim 26, wherein the first position is a proximal position and the second position is a distal position.

28. The surgical instrument of claim 26, wherein the actuation lockout system comprises:
one or more locking surfaces associated with the fastener driver; and
a control surface, wherein the control surface is aligned with a path of travel of the one or more locking surfaces when the actuation lockout system is in the locked configuration.

29. The surgical instrument of claim 28, wherein moving the actuation lockout system from the locked configuration to the unlocked configuration moves the control surface out of the path of travel of the one or more locking surfaces.

30. The surgical instrument of claim 29, wherein the control surface is disposed on a first link operatively coupled to the trigger.

31. The surgical instrument of claim 28, wherein moving the actuation lockout system from the locked configuration to the unlocked configuration moves the locking surfaces out of alignment with the control surface.

32. A surgical instrument comprising:
- a power transmission including a trigger and a fastener driver operatively coupled to the trigger, wherein actuation of the trigger from a first configuration to a second configuration moves the fastener driver between at least a first position and a second position, wherein the first configuration of the trigger is an unactuated configuration and the second configuration of the trigger is a fully actuated configuration;
- one or more locking surfaces associated with the fastener driver; and
- a control surface that is moved between a locked configuration and an unlocked configuration when the trigger is actuated from the first configuration towards the second configuration, wherein the control surface obstructs motion of at least one of the one or more locking surfaces to maintain the fastener driver in the first position when the control surface is in the locked configuration.

33. The surgical instrument of claim 32, wherein the control surface is aligned with a path of travel of the at least one of the one or more locking surfaces when the control surface is in the locked configuration.

34. The surgical instrument of claim 33, wherein moving the control surface to the unlocked configuration moves the control surface out of the path of travel of the at least one of the one or more locking surfaces.

35. The surgical instrument of claim 32, wherein the one or more locking surfaces extend outward relative to an axial direction of the fastener driver, wherein the control surface moves in a direction parallel to an axial direction of the fastener driver.

36. The surgical instrument of claim 32, wherein the first position is a proximal position and the second position is a distal position.

37. The surgical instrument of claim 32, wherein the one or more locking surfaces and the control surface comprise corresponding tabs or shoulders.

* * * * *